US009040093B2

(12) United States Patent
Wagner

(10) Patent No.: US 9,040,093 B2
(45) Date of Patent: May 26, 2015

(54) BONE GRAFT MATERIALS CONTAINING CALCIUM PHOSPHATE AND CHITOSAN

(71) Applicant: Orthovita, Inc., Malvern, PA (US)

(72) Inventor: Kristi L. Wagner, Coatesville, PA (US)

(73) Assignee: Orthovita, Inc., Malvern, PA (US)

( * ) Notice: Subject to any disclaimer, the term of this patent is extended or adjusted under 35 U.S.C. 154(b) by 91 days.

(21) Appl. No.: 13/801,044

(22) Filed: Mar. 13, 2013

(65) Prior Publication Data
US 2014/0271914 A1 Sep. 18, 2014

(51) Int. Cl.
*A61K 33/42* (2006.01)
*A61K 31/722* (2006.01)
*A61K 38/39* (2006.01)

(52) U.S. Cl.
CPC ............... *A61K 33/42* (2013.01); *A61K 31/722* (2013.01); *A61K 38/39* (2013.01)

(58) Field of Classification Search
CPC ...... A61K 33/42; A61K 31/722; A61K 38/39
See application file for complete search history.

(56) References Cited

U.S. PATENT DOCUMENTS

| | | | |
|---|---|---|---|
| 4,326,532 A | 4/1982 | Hammar | |
| 4,365,050 A | 12/1982 | Ivani | |
| 4,447,562 A | 5/1984 | Ivani | |
| 5,053,212 A * | 10/1991 | Constantz et al. | 423/305 |
| 5,064,653 A | 11/1991 | Sessions et al. | |
| 5,065,752 A | 11/1991 | Sessions et al. | |
| 5,180,426 A * | 1/1993 | Sumita | 106/35 |
| 5,254,301 A | 10/1993 | Sessions et al. | |
| 5,281,404 A * | 1/1994 | Sumita | 423/305 |
| 5,326,350 A | 7/1994 | Li | |
| 5,462,990 A | 10/1995 | Hubbell et al. | |
| 5,571,181 A | 11/1996 | Li | |
| 5,573,934 A | 11/1996 | Hubbell et al. | |
| 5,773,577 A | 6/1998 | Cappello | |
| 5,817,303 A | 10/1998 | Stedronsky et al. | |
| 5,858,746 A | 1/1999 | Hubbell et al. | |
| 5,916,928 A | 6/1999 | Sessions et al. | |
| 5,944,754 A | 8/1999 | Vacanti | |
| 5,968,542 A | 10/1999 | Tipton | |
| 6,033,654 A | 3/2000 | Stedronsky et al. | |
| 6,054,122 A | 4/2000 | MacPhee et al. | |
| 6,056,970 A | 5/2000 | Greenawalt et al. | |
| 6,096,309 A | 8/2000 | Prior et al. | |
| 6,117,425 A | 9/2000 | MacPhee et al. | |
| 6,156,305 A | 12/2000 | Brauker et al. | |
| 6,162,241 A | 12/2000 | Coury et al. | |
| 6,197,325 B1 | 3/2001 | MacPhee et al. | |
| 6,214,048 B1 * | 4/2001 | Ito et al. | 623/16.11 |
| 6,280,727 B1 | 8/2001 | Prior et al. | |
| 6,383,519 B1 | 5/2002 | Sapieszko et al. | |
| 6,413,539 B1 | 7/2002 | Shalaby | |
| 6,423,333 B1 | 7/2002 | Stedronsky et al. | |
| 6,447,802 B2 | 9/2002 | Sessions et al. | |
| 6,451,301 B1 | 9/2002 | Sessions et al. | |
| 6,458,889 B1 | 10/2002 | Trollsas et al. | |
| 6,465,001 B1 | 10/2002 | Hubbell et al. | |
| 6,495,127 B1 | 12/2002 | Wallace et al. | |
| 6,503,527 B1 | 1/2003 | Whitmore et al. | |
| 6,521,246 B2 | 2/2003 | Sapieszko et al. | |
| 6,536,448 B2 | 3/2003 | McDevitt et al. | |
| 6,559,119 B1 | 5/2003 | Burgess et al. | |
| 6,568,398 B2 | 5/2003 | Cohen | |
| 6,632,446 B1 | 10/2003 | Hubbell et al. | |
| 6,699,484 B2 | 3/2004 | Whitmore et al. | |
| 6,833,408 B2 | 12/2004 | Sehl et al. | |
| 7,008,392 B2 | 3/2006 | Beaudry | |
| 7,019,191 B2 | 3/2006 | Looney et al. | |
| RE39,192 E | 7/2006 | MacPhee et al. | |
| 7,078,055 B2 | 7/2006 | Sessions et al. | |
| 7,078,056 B2 | 7/2006 | Sessions et al. | |
| RE39,298 E | 9/2006 | MacPhee et al. | |
| 7,109,163 B2 | 9/2006 | Pendharkar et al. | |
| RE39,321 E | 10/2006 | MacPhee et al. | |
| 7,153,519 B2 | 12/2006 | Hubbell et al. | |
| 7,166,570 B2 | 1/2007 | Hunter et al. | |
| 7,186,684 B2 | 3/2007 | Pendharkar et al. | |
| 7,189,263 B2 | 3/2007 | Erbe et al. | |
| 7,189,410 B1 | 3/2007 | Drohan et al. | |
| 7,196,054 B1 | 3/2007 | Drohan et al. | |
| 7,208,179 B1 | 4/2007 | Drohan et al. | |
| 7,229,959 B1 | 6/2007 | Drohan et al. | |
| 7,252,837 B2 | 8/2007 | Guo et al. | |
| 7,279,177 B2 | 10/2007 | Looney et al. | |
| 7,294,334 B1 | 11/2007 | Michal et al. | |
| 7,300,663 B2 | 11/2007 | Stedronsky et al. | |
| 7,371,403 B2 | 5/2008 | McCarthy et al. | |

(Continued)

OTHER PUBLICATIONS

Moreau, Jennifer L., Michael D. Weir, and Hockin HK Xu. "Self-setting collagen—calcium phosphate bone cement: Mechanical and cellular properties."Journal of Biomedical Materials Research Part A 91.2 (2009): 605-613.*
Ito, M. "In vitro properties of a chitosan-bonded hydroxyapatite bone-filling paste." Biomaterials 12.1 (1991): 41-45.*
Leffler et al., "Influence of the acid type on the physical and drug liberation properties of chitosan—gelatin sponges", International Journal of Pharmaceutics, 194, pp. 229-237, 2000.
Kingery, W. D., Introduction to Ceramics, Wiley Series on the Science and Technology of Materials, 1st Ed., Hollowman, J. H., et al. (Eds.), Wiley & Sons, 1960, p. 409-417.

*Primary Examiner* — Kevin S Orwig
*Assistant Examiner* — Peter Anthopolos
(74) *Attorney, Agent, or Firm* — Lerner, David, Littenberg, Krumholz & Mentlik, LLP

(57) ABSTRACT

Described herein are materials and methods for increasing the osteoconductivity of a bone graft material, reducing the risk of infection at a surgical site, and increasing hemostasis. The bone graft materials described herein contain calcium phosphate and a form of chitin. In another embodiment the bone graft materials further comprises collagen. Chitin has been demonstrated to provide increased rate of new calcium phosphate growth, increased hemostasis, as well as antimicrobial properties. Various methods for manufacturing the bone graft materials described herein are also contemplated.

15 Claims, 11 Drawing Sheets

(56) References Cited

U.S. PATENT DOCUMENTS

| | | |
|---|---|---|
| 7,482,503 B2 | 1/2009 | Gregory et al. |
| 7,595,043 B2 | 9/2009 | Hedrick et al. |
| 7,615,373 B2 | 11/2009 | Simpson et al. |
| 7,622,437 B2 | 11/2009 | Morrissey et al. |
| 7,625,585 B2 | 12/2009 | Sessions et al. |
| 7,641,643 B2 | 1/2010 | Michal et al. |
| 7,709,005 B2 | 5/2010 | Sessions et al. |
| 7,718,412 B2 | 5/2010 | Pendharkar et al. |
| 7,744,913 B2 | 6/2010 | Noyes |
| 7,820,872 B2 | 10/2010 | Gregory et al. |
| 2011/0118850 A1 | 5/2011 | Govil et al. |

\* cited by examiner

0 Days

Calcium Phosphate Only

Calcium Phosphate and Chitosan

Chitosan alginate spheres Suspended in collagen 0.5g Knox gelatin and 6mL chitosan solution

BONE GRAFT MATERIALS CONTAINING CALCIUM PHOSPHATE AND CHITOSAN

BACKGROUND OF THE INVENTION

There has been a need for bone graft materials with improved osteogenic properties, i.e., bone graft materials that are capable of promoting bone formation. Ideally, the bone graft materials would serve as an osteoconductive scaffold that promotes the in-growth of new bone. As bone growth is promoted and increases, the bone graft material resorbs and is eventually replaced with new bone.

Chitin, the main constituent of the crustacean shells, is a naturally occurring linear polysaccharide composed of randomly distributed b-(1-4)-linked D-glucosamine (deacetylated unit) and N-acteyl-D-glucosamine (acetylated unit). Chitosan is synthetically produced by near complete deacetylation of the N-acteyl-D-glucosamine unit of chitin rendering it soluble in most acids. Chitin has been found to have an acceleratory effect on the wound healing process by increasing the rate of blood clotting at the wound site. Various forms of chitin including fibers, non-woven mats, sponges, and films have been used in wound healing products and show an increase in wound healing by over 30%. Chitosan has also been demonstrated to exhibit antimicrobial properties on various types of microorganisms.

However, there is a need for a bone graft material comprising chitosan which exhibits osteoconductive, hemostatic, and antibacterial properties without altering the structural integrity and/or handling characteristics of the bone graft material.

BRIEF SUMMARY OF THE INVENTION

Described herein are bone graft materials with improved osteoconductive properties that also exhibit improved hemostasis as well as reducing the risk of infection at the surgical site. In one embodiment the bone graft material comprises calcium phosphate and a form of chitin, for example, chitosan. It has been discovered that chitin acts as an osteoconductive agent, increasing the rate of new calcium phosphate growth which is indicative of new bone formation. Without being bound by a particular theory, it is believed that bone and blood cell adhesion to the bone graft material is affected by the charge state of the chitin. A negative charge on the bone and blood cells causes them to adhere more readily to a positive charge on the chitin. In addition, the addition of chitin to the bone graft material can add this positive charge to the bone graft material without effecting the porosity of the material, allowing bone and blood cells to infiltrate. Furthermore, it has been discovered that chitin can be incorporated into the scaffold of bone graft materials without altering the structure (e.g., porosity) of the bone graft material while retaining optimal handling characteristics (e.g., flexibility, moldability).

In one embodiment, the bone graft material contains calcium phosphate and chitosan wherein the weight ratio of chitosan to calcium phosphate is about 20:80 to about 80:20.

In another embodiment the bone graft material further comprises collagen wherein the weight ratio of collagen is about 10% to about 30% of the total bone graft material composition.

The bone graft materials described herein can be used for increasing osteogenesis by placing in the bone, at a site to be restored or repaired, the biocompatible bone graft materials described herein. While the bone graft materials comprising chitosan exhibit increased osteogenic properties they also exhibit increased hemostasis as well as reduce the risk of infection at the surgical site.

Various methods for manufacturing the bone graft materials described herein are also contemplated. In one embodiment the method for preparing a biocompatible bone graft material comprising calcium phosphate and chitin includes making a solution of acid in water; adding chitosan to the acid solution to create a slurry; incubating the slurry; optionally, adjusting the pH of the slurry with a base to a neutral pH; adding calcium phosphate and optionally collagen to the slurry to create a mixture; incubating the mixture; drying the mixture; and, optionally washing the dried mixture to form a biocompatible bone graft material comprising calcium phosphate, chitosan, and optional collagen.

In one embodiment, the concentration of acid in water is about 1% to about 20% volume by volume. In another embodiment, the concentration of chitosan when added to the acid solution is about 0.5% to about 20% weight by volume. In yet another embodiment, the mixture of calcium phosphate and chitosan-acid slurry contains a ratio of calcium phosphate to chitosan slurry of about 0.01 grams calcium phosphate per about 1 ml of chitosan slurry to about 1 grams calcium phosphate per about 1 ml of chitosan slurry.

For embodiments in which the bone graft material also comprises collagen, the collagen can be added along with calcium phosphate to the chitosan-acid slurry or can be added after the calcium phosphate and chitosan mixture is dried.

DETAILED DESCRIPTION

Figure 1:
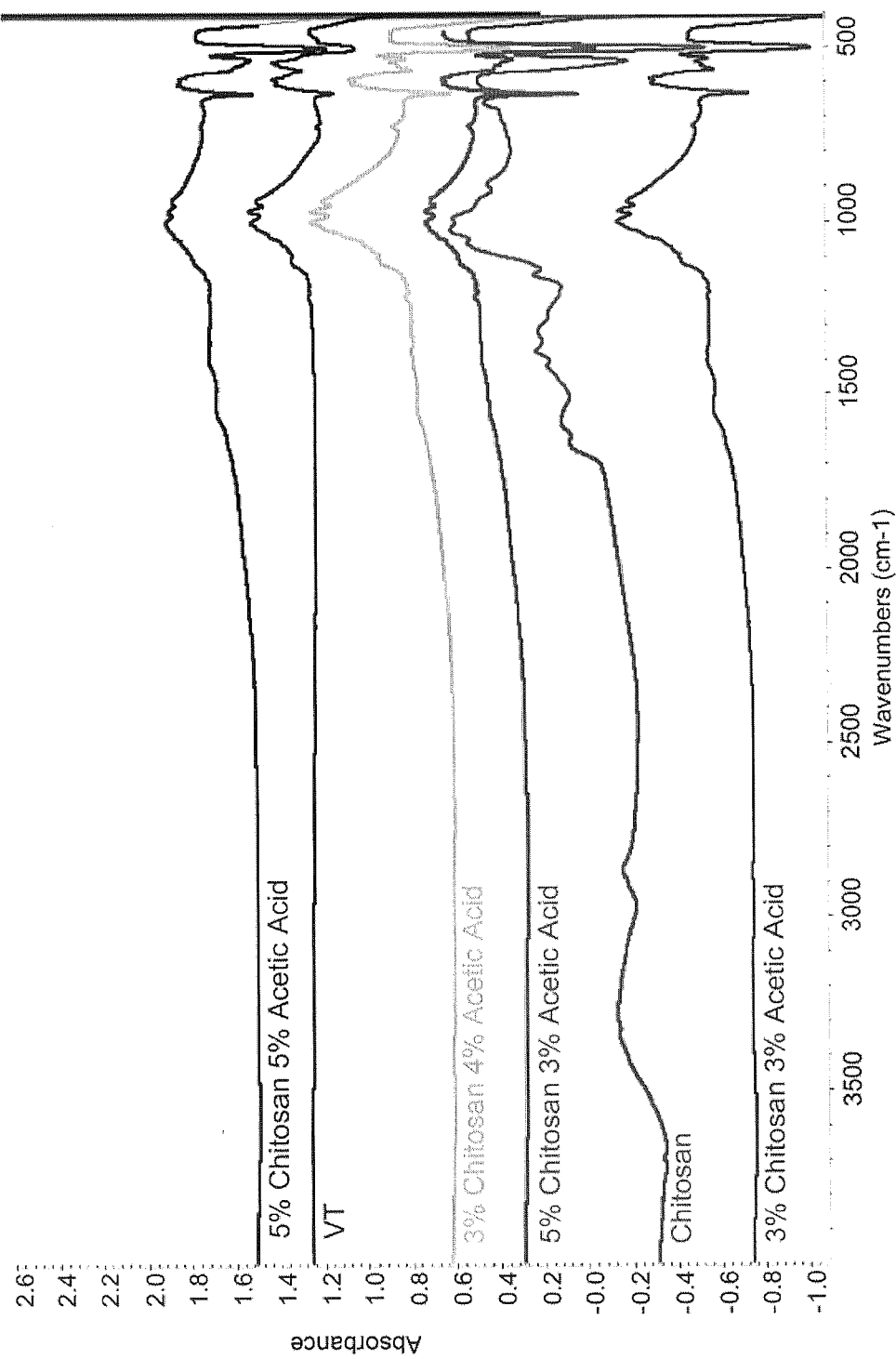
FIG. 1 summarizes the results of Fourier-Transform Infrared Spectroscopy (FTIR) analysis of various bone graft materials containing calcium phosphate and chitosan.

The invention will be described in more detail below.

While the specification concludes with the claims particularly pointing out and distinctly claiming the invention, it is believed that the invention described herein will be better understood from the following description. All temperatures are in degrees Celsius unless specified otherwise. The invention described herein can comprise (open ended) or consist essentially of the components of the invention described herein as well as other ingredients or elements described herein. As used herein, "comprising" means the elements recited, or their equivalent in structure or function, plus any other element or elements which are not recited. The terms "having," "including," and "comprised of" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Generally, such additives may not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

It should be further understood that a description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.3, 3, 4, 5, 5.7 and 6. This applies regardless of the breadth of the range.

Bone Graft Materials Containing Calcium Phosphate and Chitosan

Described herein are biocompatible bone graft materials for use in restoring or repairing a defect at a bony site that exhibits increased osteogenic properties, increased hemostasis, and reduced the risk of infection at the surgical site. In one embodiment, the biocompatible bone graft materials described herein comprise a calcium salt and a form of chitin.

It has been discovered that chitin acts as an osteoconductive agent, increasing the rate of new calcium phosphate growth which is indicative of new bone formation. Without being bound by a particular theory, it is believed that bone and blood cell adhesion to the bone graft material is affected by the charge state of the chitin. A negative charge on the bone and blood cells causes them to adhere more readily to a positive charge on the chitin. In addition, the addition of chitin to the bone graft material can add this positive charge to the bone graft material without effecting the porosity of the material, allowing bone and blood cells to infiltrate. In addition, the bone graft materials described herein containing chitin also exhibit increased hemostasis as well as antimicrobial properties.

Various forms of chitin are contemplated and include, for example, deacetylated chitin, e.g., chitosan, as well as other linear polysaccharides. Also contemplated are alpha, beta, and gamma forms of chitin. However, for the sake of brevity, "chitosan" includes any form of chitin known to those skilled in the art.

Various calcium salts are contemplated and include, for example, calcium phosphates such as tricalcium phosphate, β-tricalcium phosphate (β-TCP), α-tricalcium phosphate (α-TCP), and apatites such as hydroxyapatite. However, for the sake of brevity, "calcium phosphate" includes any calcium salt known to those skilled in the art. The preparation of various forms of calcium phosphate for use in the present invention is described in U.S. Pat. Nos. 6,383,519 and 6,521,246, assigned to the assignee of the present invention and incorporated herein by references in their entireties. An exemplary calcium phosphate product is Vitoss® Bone Graft Substitute (Orthovita, Inc., Malvern, Pa.).

In one embodiment the calcium phosphate is β-TCP. In typical embodiments the calcium phosphate is porous. In another embodiment, the calcium phosphate contains micro-, meso-, and macroporosity. In yet another embodiment the porosity of the calcium phosphate is interconnected. Macroporosity is characterized by pore diameters greater than about 100 μm and, in some embodiments, up to about 1000 μm to 2000 μm. Mesoporosity is characterized by pore diameters between about 100 μm and 10 μm, while microporosity occurs when pores have diameters below about 10 μm. It is preferred that macro-, meso-, and microporosity occur simultaneously and are interconnected in products of the invention. It is not necessary to quantify each type of porosity to a high degree. Rather, persons skilled in the art can easily determine whether a material has each type of porosity through examination, such as through the preferred methods of mercury intrusion porosimetry, helium pycnometry and scanning electron microscopy. While it is certainly true that more than one or a few pores within the requisite size range are needed in order to characterize a sample as having a substantial degree of that particular form of porosity, no specific number or percentage is called for. Rather, a qualitative evaluation by persons skilled in the art shall be used to determine macro-, meso-, and microporosity.

In one embodiment, the calcium phosphate is in the form of particles or morsels and may contain a porous structure as described herein.

It will be appreciated that in some embodiments of materials prepared in accordance with this invention the overall porosity will be high. This characteristic is measured by pore volume, expressed as a percentage. Zero percent pore volume refers to a fully dense material, which, perforce, has no pores at all. One hundred percent pore volume cannot meaningfully exist since the same would refer to "all pores" or air. Persons skilled in the art understand the concept of pore volume, however and can easily calculate and apply it. For example, pore volume may be determined in accordance with Kingery, W. D., Introduction to Ceramics, Wiley Series on the Science and Technology of Materials, $1^{st}$ Ed., Hollowman, J. H., et al. (Eds.), Wiley & Sons, 1960, p. 409-417, who provides a formula for determination of porosity. Expressing porosity as a percentage yields pore volume. The formula is: Pore Volume=$(1-f_p)$ 100%, where $f_p$ is fraction of theoretical density achieved.

Porosity can be measured by Helium Pycnometry. This procedure determines the density and true volume of a sample by measuring the pressure change of helium in a calibrated volume. A sample of known weight and dimensions is placed in the pycnometer, which determines density and volume. From the sample's mass, the pycnometer determines true density and volume. From measured dimensions, apparent density and volume can be determined. Porosity of the sample is then calculated using (apparent volume-measured volume)/apparent volume. Porosity and pore size distribution may also be measured by mercury intrusion porosimetry.

Pore volumes in excess of about 30% may be achieved in accordance with this invention while materials having pore volumes in excess of 50% or 60% may also be routinely attainable. Some embodiments of the invention may have pore volumes of at least about 70%. Some embodiments that may be preferred have pore volumes in excess of about 75%, with 80% being still more preferred. Pore volumes greater than about 90% are possible as are volumes greater than about 92%. In some preferred cases, such high pore volumes are attained while also attaining the presence of macro- meso-, and microporosity as well as physical stability of the materials produced. It is believed to be a great advantage to prepare graft materials having macro-, meso-, and microporosity simultaneously with high pore volumes that also retain some compression resistance and flexibility when wetted.

In one embodiment, the bone graft material comprises porous calcium phosphate morsels at a size greater than about 0.25 mm. The morsels of calcium phosphate may be, for example, about 1-2 mm in size for some embodiments or about 0.25 mm to about 1 mm or to about 2 mm for other embodiments of the present invention. For flowable compositions, it will be appreciated that the morsel size will be selected considering the desired delivery apparatus. For example, for delivery of a flowable composition using a standard syringe, it will be necessary to select a morsel size that fits through the syringe orifice.

Due to the high porosity and broad pore size distribution (1 μm to 1000 μm) of the present invention graft, the implant is not only able to wick/soak/imbibe materials very quickly, but is also capable of retaining them. A variety of fluids could be used with the present invention including blood, bone marrow aspirate, saline, antibiotics and proteins such as bone morphogenetic proteins (BMPs). Materials of the present invention can also be imbibed with cells (e.g., fibroblasts, mesenchymal, stromal, marrow and stem cells), platelet rich plasma, other biological fluids, and any combination of the above. Bone grafts of the present invention actually hold, maintain, and/or retain fluids once they are imbibed, allowing for contained, localized delivery of imbibed fluids. This capability has utility in cell-seeding, drug delivery, and delivery of biologic molecules as well as in the application of bone tissue engineering, orthopaedics, and carriers of pharmaceuticals.

Wettability determines the amount of fluid taken up by sample material and if the material absorbs an appropriate amount of fluid within a specified time. Pieces of the material are randomly selected, weighed, and placed in a container of fluid for 120 seconds. If the samples adequately take up fluid, they are then weighed again to determine the percentage of mass increase from fluid absorption. Some embodiments exhibit a wettability wherein bone graft material becomes fully saturated within 120 seconds with at least a 100% mass increase. In some embodiments, the graft material experiences a 150% mass increase and yet, in others, an approximate 200%-300% mass increase. Fluids that may be used in the present invention may be bone marrow aspirate, blood, saline, antibiotics and proteins such as bone morphogenetic proteins (BMPs) and the like.

It is preferred that flexible grafts of the present invention will be able to wick and hold fluids, even under compression. It is preferred that moldable embodiments will be able to wick and hold fluids, even in a wet environment. For example, if a wetted, flexible graft is placed on mesh suspended above a weigh boat and is challenged with a 500 g weight, it is preferred that the graft maintain a mass of fluid at least about 95% of the mass of the graft or about equivalent to the mass of the graft. If a wetted, moldable graft of the invention is placed in fluid, it is preferred that the graft maintains as a continuous object and does not swell substantially larger in size than its original dimensions. In some instances, the graft does not swell in size greater than about 50% more than its original dimensions, by qualititative assessment. If a wetted, moldable graft of the invention is compressed, it is preferred that the graft maintain a mass of fluid at least about 85% of the mass of the graft or about equivalent to the mass of the graft. Bone graft materials of the present invention have osteoconductive and osteostimulatory properties. In certain embodiments, the addition of bioactive glass in the present invention enhances the ability of the product to foster bone growth. The bone graft materials of the present invention may also have osteoinductive properties.

In one embodiment, the bone graft material comprises calcium phosphate and chitosan. The weight ratio of chitosan to calcium phosphate is not limited. In one embodiment, the weight ratio of chitosan to calcium phosphate is about 20:80 to about 80:20. In another embodiment, the weight ratio of chitosan to calcium phosphate is about 40:60 to about 70:30. In yet another embodiment, the weight ratio of chitosan to calcium phosphate is about 55:45 to about 67:33.

In one embodiment, the bone graft material comprises calcium phosphate and chitosan but does not contain collagen. Chitin, including chitosan, increases the viscosity of the calcium phosphate upon mixing without the need for adding a viscosity modifying agent, such as collagen. Unlike typical bone graft materials in the art that require the addition of collagen, gelatin, or other similar polymers to create a putty-like or moldable bone graft, the bone graft materials described herein containing calcium phosphate and chitosan without collagen exhibit a putty-like substance that is moldable, moderately flexible, and easily compressed.

It is also contemplated that the various forms of chitin described herein can be used to coat or can be combined with other materials known in the art for preparing bone graft materials or bone implants. Such materials include, for example, collagen, metals including titanium, stainless steel and cobalt, polymers including polymethylmethacrylate (PMMA), and other similar hardenable bone cement and bone augmentation materials, including those sold under the trademark Cortoss® (Orthovita, Malvern, Pa.).

In one embodiment, the bone graft material contains calcium phosphate, chitosan, and collagen. Collagen is added in order to provide a bone graft material with a more cohesive mass, such as, for example, a sponge-like material. In one embodiment the biocompatible bone graft material comprises a homogenous blend of calcium phosphate and collagen. In another embodiment the bone graft material comprises collagen wherein the weight ratio collagen is about 10% to about 30% of the total bone graft material composition. In yet another embodiment the bone graft material comprises collagen wherein the weight ratio collagen is about 15% to about 25% of the total bone graft material composition.

Collagens suitable for use in the present invention may consist of non-crosslinked collagen pellet, lyophilized non-cross-linked collagen, and cross-linked collagen. Suitable collagens are described, for example, in U.S. Pat. No. 7,189, 263, which is herein incorporated by reference in its entirety. Some embodiments of the present invention contain collagen that comprises up to 100% Type I collagen. In other embodiments, the collagens used may be predominantly, or up to about 90%, of Type I collagen with up to about 5% of Type III collagen or up to about 5% of other types of collagen. Suitable Type I collagens include native fibrous insoluble human, bovine, porcine, or synthetic collagen, soluble collagen, reconstituted collagen, and microfibrillar forms of collagen as described, for example, in U.S. Pat. Nos. 6,096,309 and 6,280,727, which are herein incorporated by reference in its entirety. The various types of collagens can be used alone or in combination.

In one embodiment the collagen is cross-linked with one selected from the group consisting of N-(3-dimethylaminopropyl-N'-ethylcarbodiimide hydrochloride and N-hydroxysuccinimde; and gluteraldehyde.

Methods of Using the Bone Graft Materials

The bone graft materials described herein may be used to increases osteogenesis, while also increasing hemostasis and reducing the rate of infection at the surgical site. These methods include, for example, placing in the bone, at a site to be restored or repaired, the biocompatible bone graft materials described herein. In one embodiment the bone graft material is wetted with a fluid prior to placement in the bony site. In another embodiment, the wetted bone graft material is flexible, moldable or flowable.

Many of the embodiments disclosed herein are to fill bony voids and defects. It will be appreciated that applications for the embodiments of the present invention include, but are not limited to, filling interbody fusion devices/cages (ring cages, cylindrical cages), placement adjacent to cages (i.e., in front cages), placement in the posterolateral gutters in posterolateral fusion (PLF) procedures, backfilling the iliac crest, acetabular reconstruction and revision hips and knees, large tumor voids, use in high tibial osteotomy, burr hole filling, and use in other cranial defects. The bone graft material strips may be suited for use in posterolateral fusion (PLF) by placement in the posterolateral gutters, and in onlay fusion grafting. Additional uses may include craniofacial and trauma procedures that require covering or wrapping of the injured/void site. The bone graft material cylinders may be suited to fill spinal cages and large bone voids, and for placement along the posterolateral gutters in the spine.

Methods of Manufacturing Bone Graft Materials

Described herein are methods for manufacturing the biocompatible bone graft materials described herein. One exemplary embodiment for preparing a bone graft material comprising calcium phosphate and chitosan includes making a solution of acid in water; adding chitosan to the acid solution to create a slurry; incubating the slurry; optionally, adjusting the pH of the slurry with a base to a neutral pH; adding calcium phosphate and, optionally, collagen to the slurry to create a mixture; incubating the mixture; drying the mixture; and optionally, washing the lyophilized material to form a biocompatible bone graft material.

Any acid can be used to make the solution of acid in water. Exemplary acids include acetic acid, acrylic acid, citric acid, formic acid, hydrochloric acid, lactic acid, and tartaric acid. There is no limit to the concentration of acid in the aqueous solution. In one embodiment, the concentration of acid in water is about 1% to about 99% volume by volume. In another embodiment, the concentration of acid in water is about 1% to about 20% volume by volume. In yet another embodiment, the concentration of acid in water is about 1% to about 10% volume by volume. In still another embodiment, the concentration of acid in water is about 1% to about 5% volume by volume.

The amount of chitosan mixed with the acid solution is not limited, so long as the temperature does not degrade or chemically modify the chitosan. In one embodiment, the concentration of chitosan in the acid solution is about 0.5% to about 20% weight by volume. In another embodiment, the concentration of chitosan in the acid solution is about 0.5% to about 10% weight by volume. In yet another embodiment, the concentration of chitosan in the acid solution is about 1% to about 5% weight by volume.

Upon addition of chitosan to the acid solution to form a slurry, the slurry of chitosan and calcium phosphate is incubated. During incubation, the slurry can be shaken, mixed, or both. The length of the incubation step is not limited. In one embodiment, incubation is about 0.5 hour to about 5 days. In another embodiment the slurry is incubated for about 4 hours to about 3 days. In yet another embodiment the slurry is incubated for about 4 hours to about 24 hours.

The temperature of the slurry during incubation is not limited so long as the components are not degraded or chemically altered. In one embodiment, the temperature of the slurry during incubation is about room temperature to about 70° C. In another embodiment, the temperature of the slurry during incubation is about 37° C. to about 50° C.

After incubating the chitosan-acid slurry, the pH of the slurry can optionally be adjusted to a neutral pH with any base. A neutral pH is a pH of at least about 4 to about 8. Adjusting the pH to a neutral pH may help to maintain the biocompatibility of the bone graft material. Any base known to those skilled in the art can be used to adjust the pH of the slurry including, for example, sodium hydroxide (NaOH). In one embodiment, the pH is adjusted to about pH 4 to about pH 5. In certain embodiments, the pH is not adjusted with a base after incubating the chitosan-acid slurry, because upon the subsequent addition of calcium phosphate to the chitosan-acid slurry, the pH may be naturally adjusted to a neutral pH.

After incubating the slurry, or optionally adjusting the pH of the slurry, calcium phosphate is added to the slurry to create a mixture of chitosan and calcium phosphate. The ratio of chitosan to calcium phosphate is not limited. In one embodiment, the ratio of calcium phosphate to chitosan-acid slurry is about 0.01 grams per ml to about 1 gram per ml. In another embodiment, the ratio of calcium phosphate to chitosan-acid slurry is about 0.01 grams per ml to about 0.5 grams per ml. In yet another embodiment, the ratio of calcium phosphate to chitosan-acid slurry is about 0.025 grams per ml to about 0.25 grams per ml.

During incubation of the mixture of chitosan-acid slurry and calcium phosphate, the mixture can be shaken, mixed, or both. The length of the incubation is step not limited. In one embodiment, incubation is about 1 hour to about 24 hours. In another embodiment, incubation is about 1 hour to about 5 hours. The temperature at which incubation is performed is not limit so long as the components are not degraded or chemically altered. In one embodiment incubation is performed at about room temperature to about 37° C.

After mixing the calcium phosphate and optional collagen with the chitosan-acid slurry, the mixture is dried to produce a biocompatible bone graft material. Drying can occur, for example, by vacuum, by air drying, or by freezing and lyophilizing the mixture. In one embodiment, the mixture is dried by freezing and lyophilizing, wherein the freezing temperature is about −28° C. to about 0° C., and the lyophilization is performed to dryness. In another embodiment, lyophilization is performed for up to 5 days. In yet another embodiment, lyophilization is performed for up to 3 days.

Lastly, the dried bone graft material can optionally be washed with a solution, for example water, to remove any residual acid from the bone graft material. The optional washing step can occur any time subsequent to the drying step but prior to implantation into the bony site.

In one embodiment, the calcium phosphate added to the chitosan-acid slurry is in the form of particles or morsels. In one embodiment, the amount of chitosan-acid slurry added to the calcium phosphate particles or morsels, as well as incubation time, is sufficient to saturate and coat the entire surface of the calcium phosphate particles or morsels, including any porous surfaces that may exist in the calcium phosphate particles or morsels without disrupting, changing or blocking the pores of the porous surface of the particles or morsels.

For the embodiments in which the bone graft material contains collagen, the collagen can be added before drying of the mixture as described above. In another embodiment, the collagen can be added to the dried calcium phosphate and chitosan mixture to create a second mixture and incubated as described above. After incubation, the second mixture can optionally be dried a second time, as described above, to form a bone graft material comprising calcium phosphate, collagen, and chitosan.

In one embodiment, bone graft materials are contemplated that are prepared by the any of the methods described herein. For example, in one embodiment, a bone graft material comprising calcium phosphate and chitosan is prepared by making a solution of acid in water; adding chitosan to the acid solution to create a slurry; incubating the slurry; optionally, adjusting the pH of the slurry with a base to a neutral pH; combining the chitosan-acid slurry with calcium phosphate particles or morsels and, optionally, collagen to create a mixture; incubating the mixture; drying the mixture; and optionally, washing the dried material to form a biocompatible bone graft material, wherein the amount of chitosan-acid slurry added to the calcium phosphate particles or morsels, as well as incubation time, is sufficient to saturate and coat the entire surface of the calcium phosphate particles or morsels, including any porous surfaces that may exist in the calcium phosphate particles or morsels.

EXAMPLES

Example 1

Preparation of Bone Graft Materials Containing Calcium Phosphate and Chitosan Several formulations of bone graft materials were prepared with varying amounts of chitosan and acid solutions: 5% chitosan in 5% acetic acid, 3% chitosan in 3% acetic acid, 3% chitosan in 4% acetic acid, and 5% chitosan in 3% acetic acid using the following method. First, the appropriate concentration of acid solution was prepared by diluting a stock solution of the acid in water. Chitosan was added to the acid solution to prepare a slurry to form the appropriate concentration of chitosan. The slurry was then mixed for at least 4 hours at room temperature. After mixing, 0.5 grams of calcium phosphate morsels were added to 20 ml of the slurry and mixed for 60 minutes at room temperature. The mixtures were then frozen and lyophilized to form a bone graft material. The resulting materials were putty-like, moderately flexible, and easily compressed.

In order to determine if the addition of chitosan to the calcium phosphate caused any chemical change to the structure of the calcium phosphate morsels, Fourier-Transform Infrared Spectroscopy (FTIR) was performed to analyze the bone graft materials. For controls, unmodified calcium phosphate and chitosan alone were also tested. The FTIR spectra results are summarized in FIG. 1 and demonstrate that there is no significant chemical change to the structure of the calcium phosphate upon addition of chitosan in any of the bone graft formulations.

Example 2

Osteoconductivity of Bone Graft Materials Containing Chitosan

A bone graft material was prepared with 1% chitosan in 2% acetic acid. First, the appropriate concentration of acid solution was prepared by diluting a stock solution of the acid in water. Chitosan was added to the acid solution to prepare a slurry to form the appropriate concentration of chitosan. The pH was then adjusted with a base to pH 4.2. After adjusting the pH enough calcium phosphate particles were added to soak up the chitosan-acid slurry in order to saturate the calcium phosphate particles and allowed to air dry overnight to form a bone graft material. After drying, approximately 0.2 g of the bone graft material was added to approximately 1 mL of mammalian cell culture broth and incubated at 37 degrees Celsius for 24 hours. After incubation, the medium was extracted and added to a culture of MG63 osteoblast, cells and Saos-2 osteoblast cells. The cells were cultured for up to 8 months. Various enzymatic tests and microscopic images were taken during this time as described below.

Figure 2:
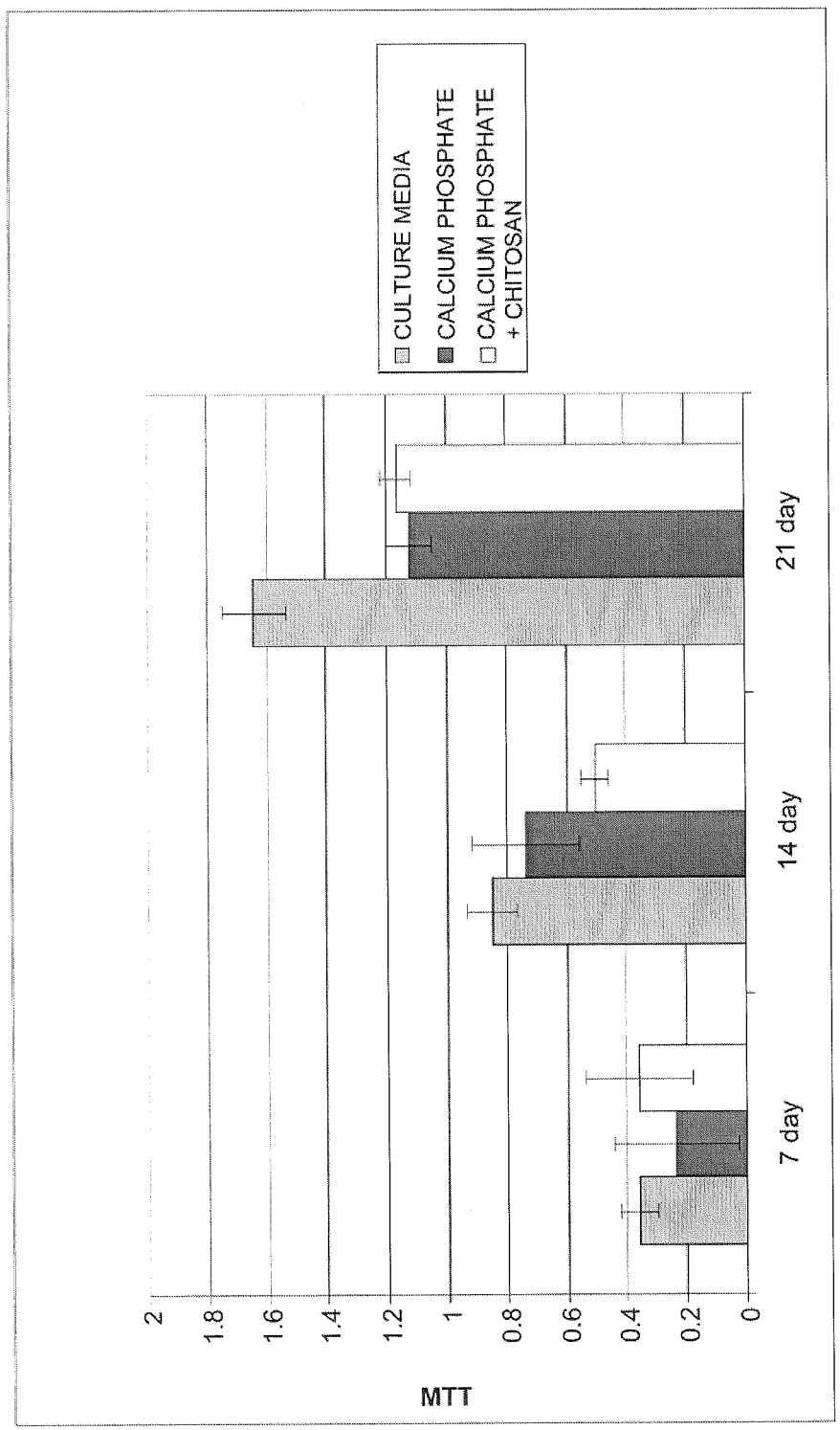
FIG. 2 summarizes the results of the MTT assay for various bone graft materials containing calcium phosphate and chitosan.

At 7 days, 14 days, and 21 days the MG63 cells were tested using an MTT assay which indicates continued cell proliferation of the MG63 cells. As a control, MG63 cells plated only with culture media was tested. The results of the MIT assay are summarized in FIG. 2 and indicate that the mammalian cells are continuing to proliferate with bone graft materials described herein containing calcium phosphate and chitosan comparable to the bone graft materials containing calcium phosphate only.

Figure 3:
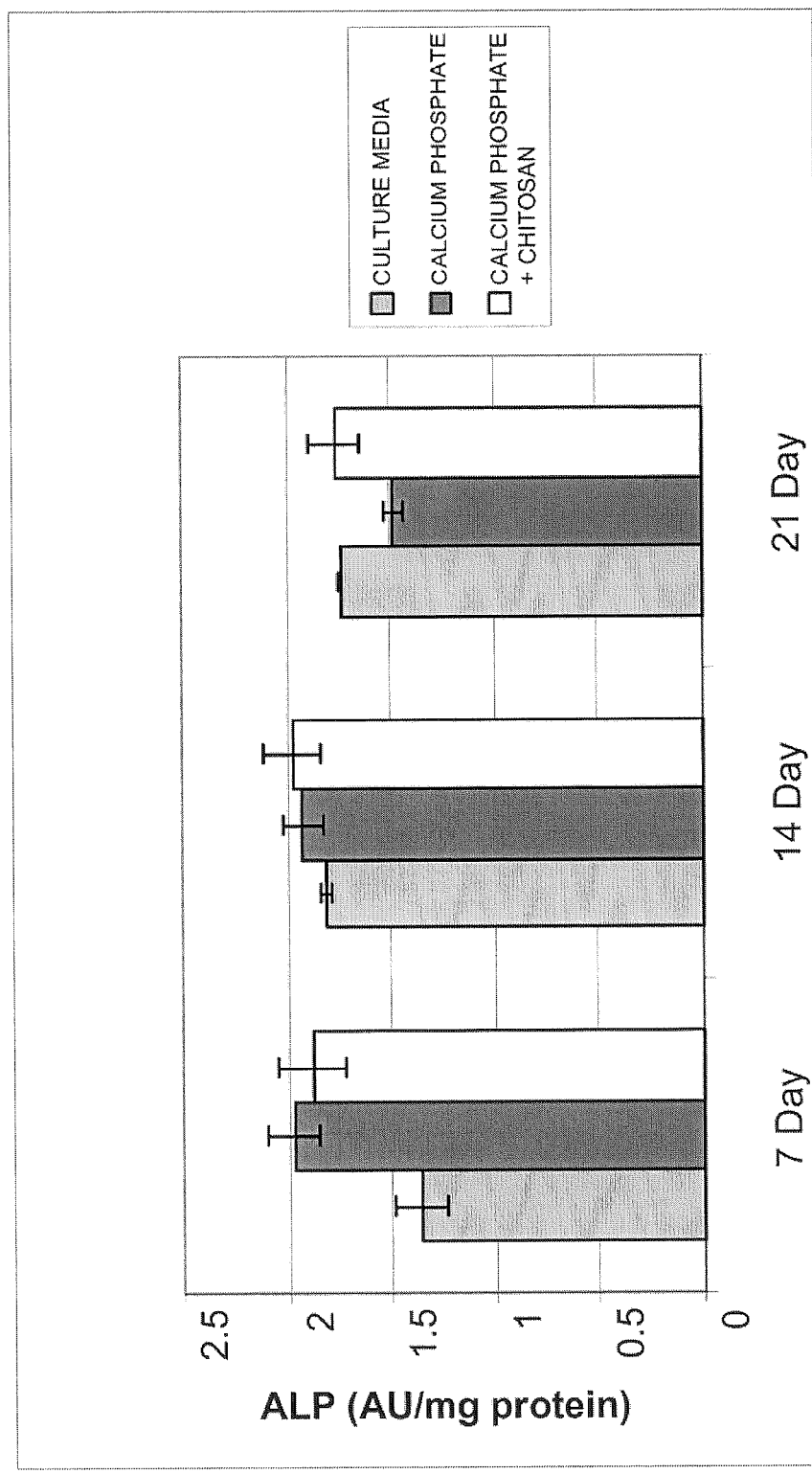
FIG. 3 summarizes the results of the ALP assay for various bone graft materials containing calcium phosphate and chitosan.

At 7 days, 14 days, and 21 days the MG63 cells were tested using an assay which is a bone differentiation marker. As a control, MG63 cells plated only with culture media were tested. The results of the ALP assay are summarized in FIG. 3 and indicate that the mammalian cells contain similar amounts, if not more, of the bone differentiation marker with bone graft materials described herein containing calcium phosphate and chitosan compared to the bone graft materials containing calcium Phosphate only, particularly at 14 and 21 days.

At 0 days, 28 days, 90 days, and 150 days, the cell proliferation and infiltration of the Saos-2 cells and new calcium phosphate formation with bone graft materials containing chitosan and calcium phosphate was observed using scanning electron microscopy images (SEM). As a control, the bone graft materials containing only calcium phosphate and not chitosan were evaluated. Selected SEM images are shown in FIG. 4-7. The results are summarized in Table 1 below and indicate a significant increase in the rate of protein matrix formation, osteoid formation, and new calcium phosphate growth within 28 days with bone graft materials containing chitosan described herein. Also noted in FIG. 4, the addition of chitosan did not alter or block the porous nature of the calcium phosphate. This allows infiltration of cells into the bone graft material in order to initiate new bone growth in an expedited manner.

TABLE 1

Figure 4:
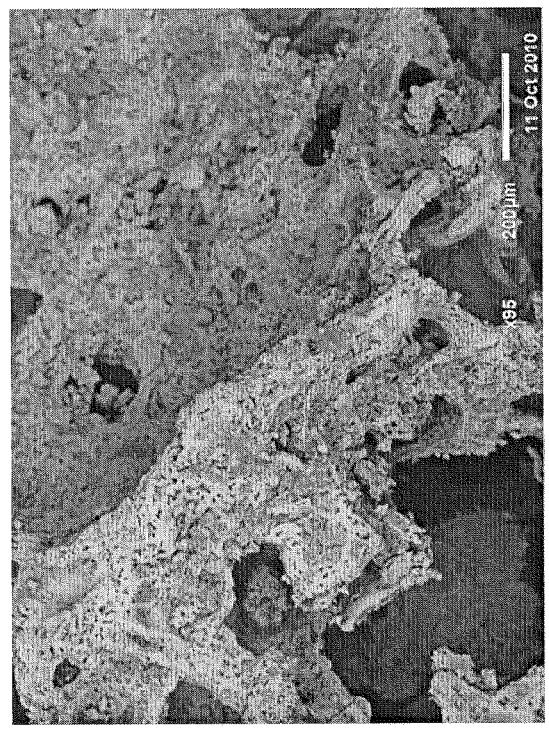
FIG. 4 contains Scanning Electron Microscopy (SEM) images of bone graft materials at 0 days.
Figure 4:
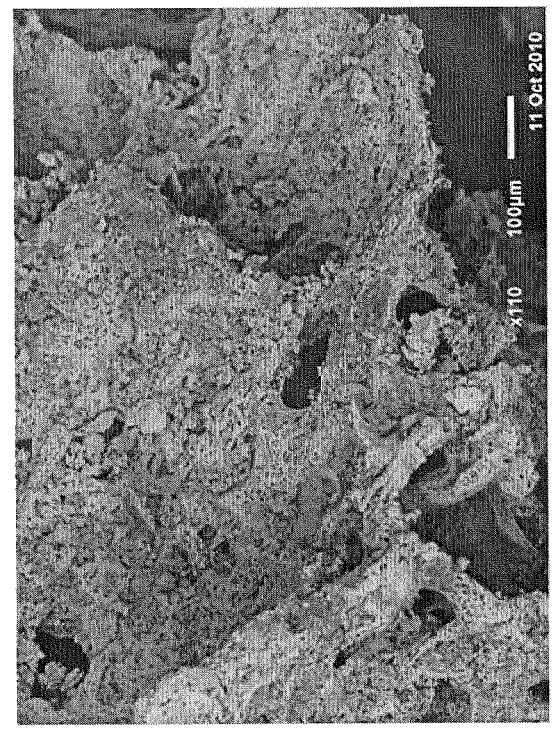
Figure 5:
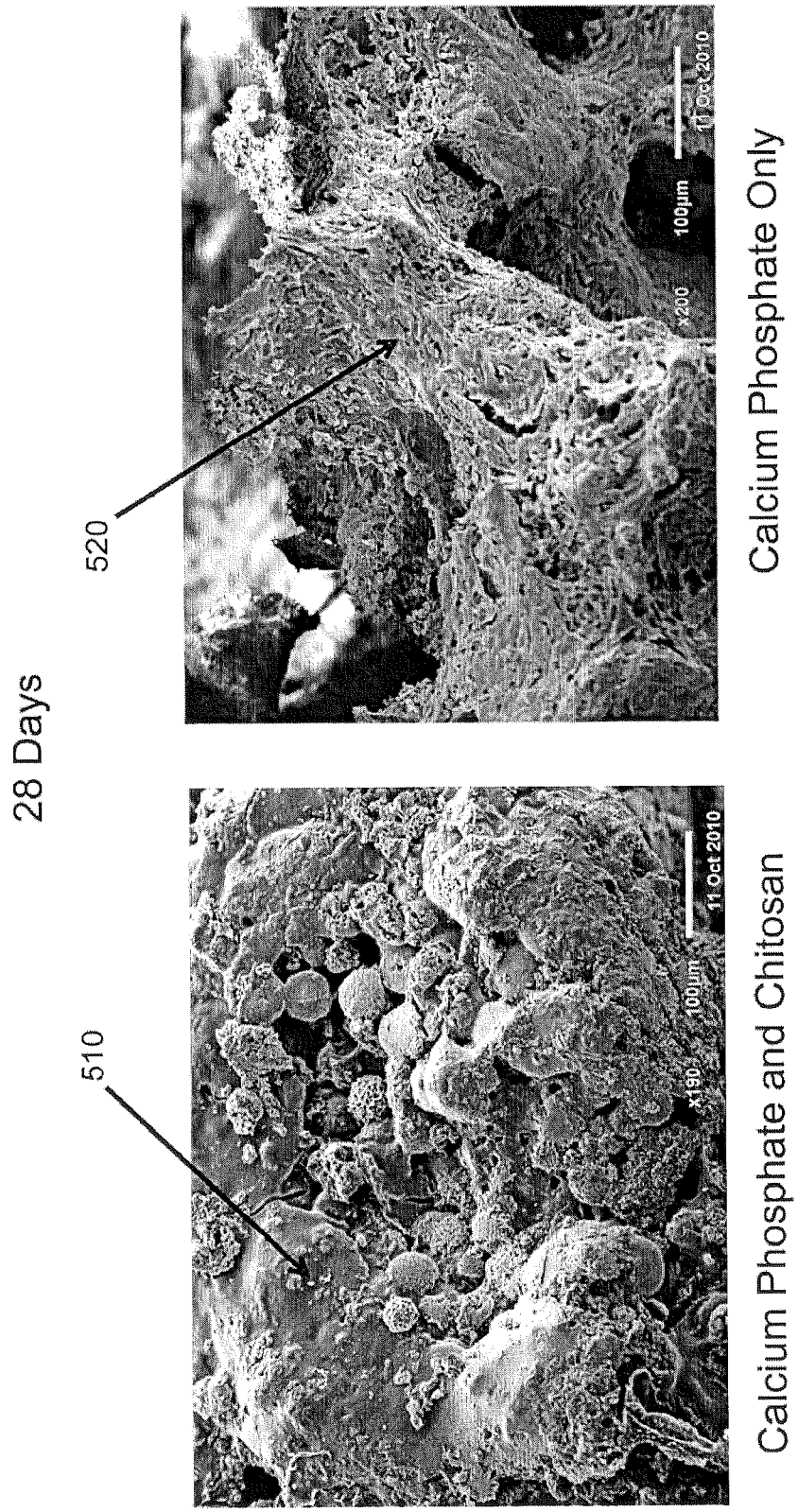
FIG. 5 contains Scanning Electron Microscopy (SEM) images of bone graft materials at 28 days.

| FIG. | Time Point | Sample | Results |
|---|---|---|---|
| FIG. 4 | 0 Days | Present invention material with calcium phosphate + chitosan | No cell growth or matrix observed; porous scaffold maintained with the addition of chitosan |
|  |  | calcium phosphate only | No cell growth or matrix observed; porous scaffold observed |
| FIG. 5 | 28 Days | Present invention material with calcium phosphate + chitosan | Osteoid cells begin to lay down protein matrix and coat scaffold surface(510); some osteoid formation |
|  |  | calcium phosphate only | Cell matrix is less confluent (520); no osteoid formation observed |

TABLE 1-continued

Figure 6:
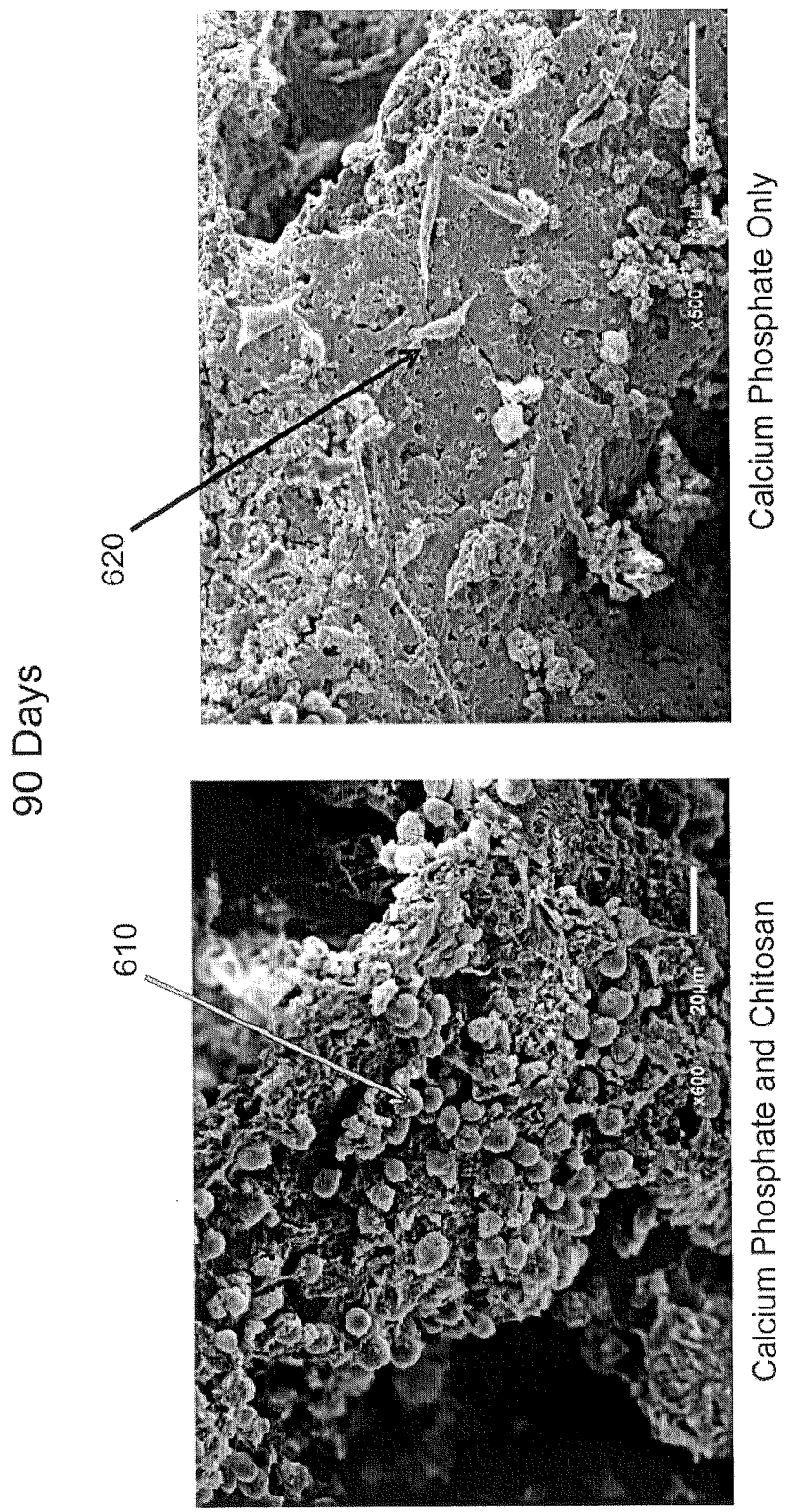
FIG. 6 contains Scanning Electron Microscopy (SEM) images of bone graft materials at 90 days.
Figure 7:
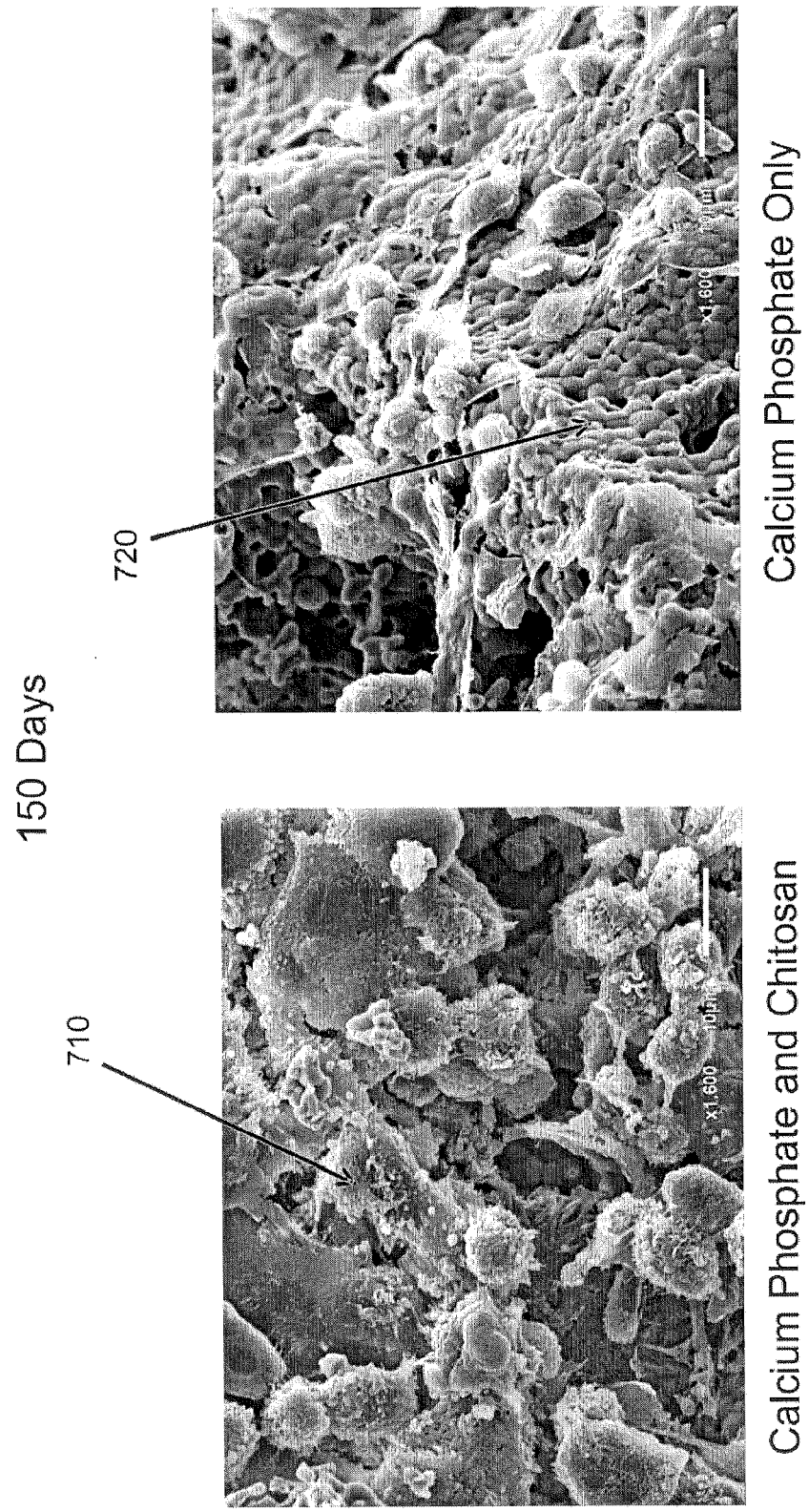
FIG. 7 contains Scanning Electron Microscopy (SEM) images of bone graft materials at 150 days.

| FIG. | Time Point | Sample | Results |
|---|---|---|---|
| FIG. 6 | 90 Days | Present invention material with calcium phosphate + chitosan | Osteoid formation observed with increased cell activity and proliferation (610) |
| | | calcium phosphate only | Osteoid formation less pronounced; osteoblast cells are elongated (620) |
| FIG. 7 | 150 Days | Present invention material with calcium phosphate + chitosan | Scaffold covered in thick protein matrix and osteoid formations; scaffold barely visible (710) |
| | | calcium phosphate only | Less osteoid formation; scaffold still visible (720) |

Figure 8:
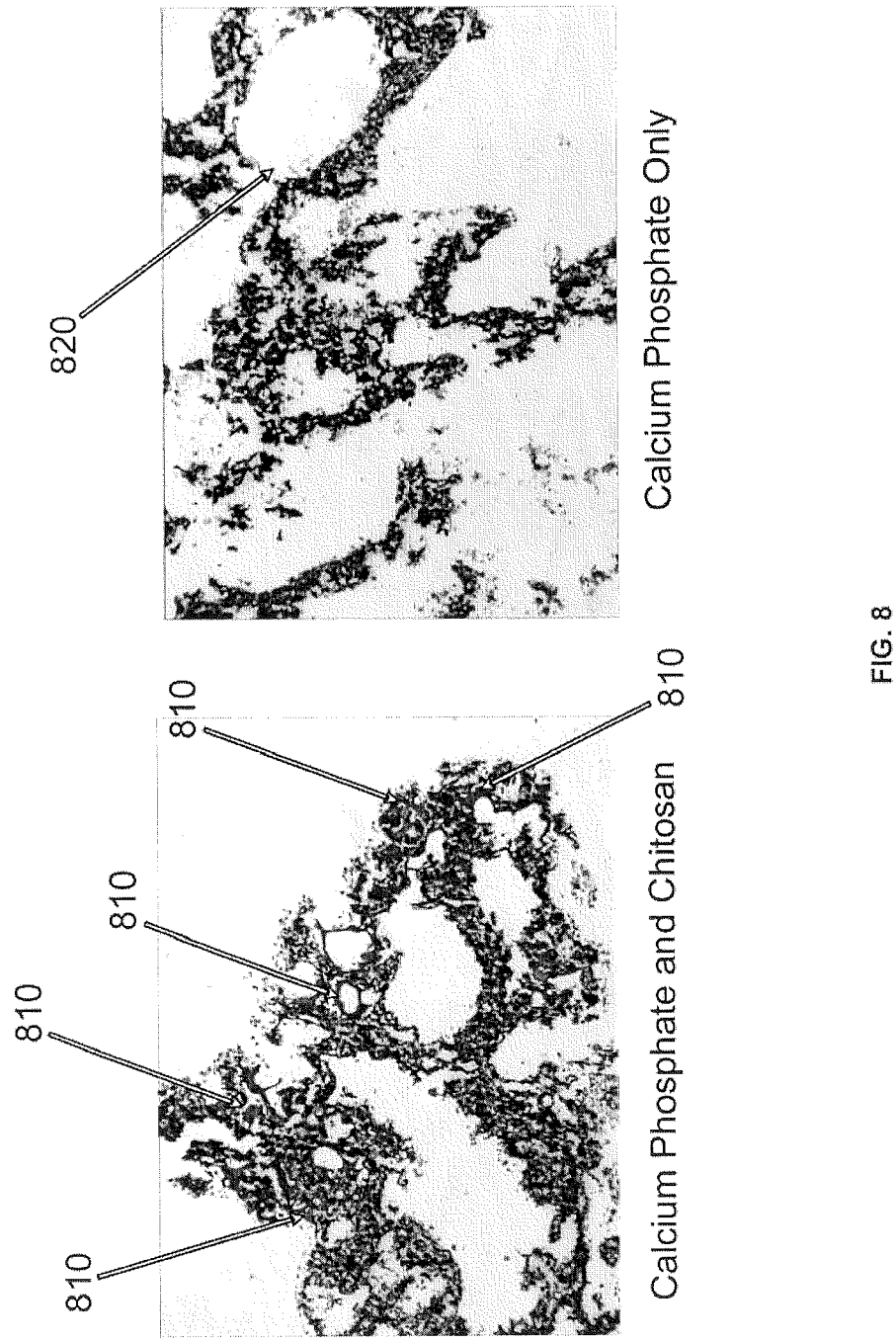
FIG. 8 contains H&E staining of bone graft materials at 90 days.

Hematoxylin and eosin (H&E) staining was performed on 90 day samples in order to determine the extent of protein matrix lining on the bone graft materials. FIG. 8 contains H&E images of bone graft materials containing chitosan and calcium phosphate or calcium phosphate only. At 90 days, the bone graft materials containing chitosan and calcium phosphate have increased matrix lining throughout the bone craft material including inside the pores indicated by the red staining of eosin (indicated with arrows and labeled "810" in FIG. 8). However, the bone graft materials without chitosan contain a significantly less matrix layer, including within the pores of the calcium phosphate (indicated as an arrow and labeled. "820" in FIG. 8). The matrix layer observed in the bone graft materials containing chitosan indicates a faster rate of infiltration of osteoid cells and initiation of new bone growth in these samples.

Figure 9:
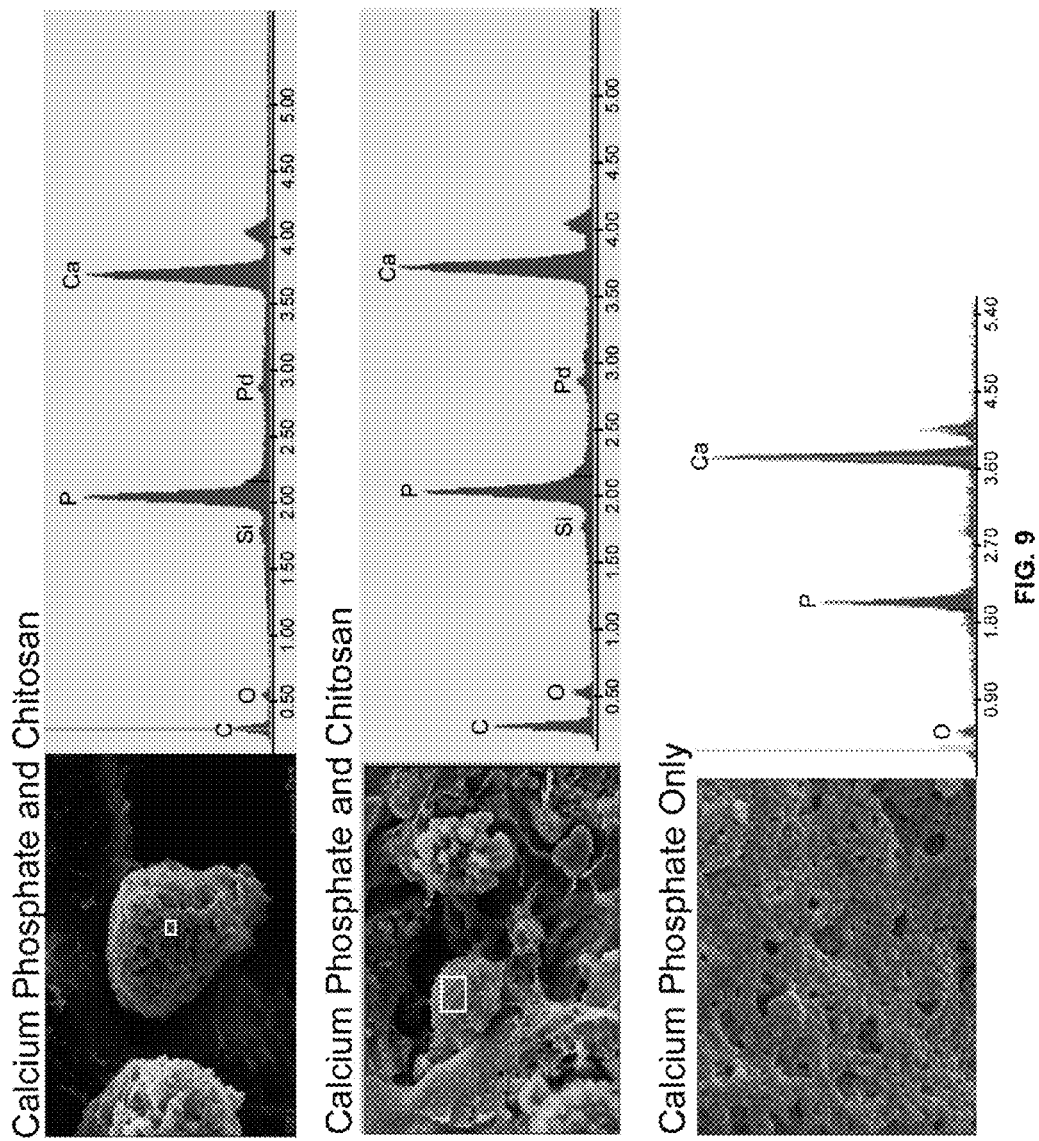
FIG. 9 contains EDAX scans of bone graft materials at 90 days.

The results of the H&E study indicating faster osteoblast infiltration and new bone growth with bone graft materials described herein containing chitosan was confirmed by Energy dispersive X-ray spectroscopy (EDAX). EDAX spectra for bone graft materials with or without chitosan at 90 days are demonstrated in FIG. 9. The large carbon (C) peaks in the bone graft materials containing chitosan indicate increased osteoblast cell proliferation compared to the bone graft material containing calcium phosphate only.

Example 3

Antimicrobial Testing

Figure 10:
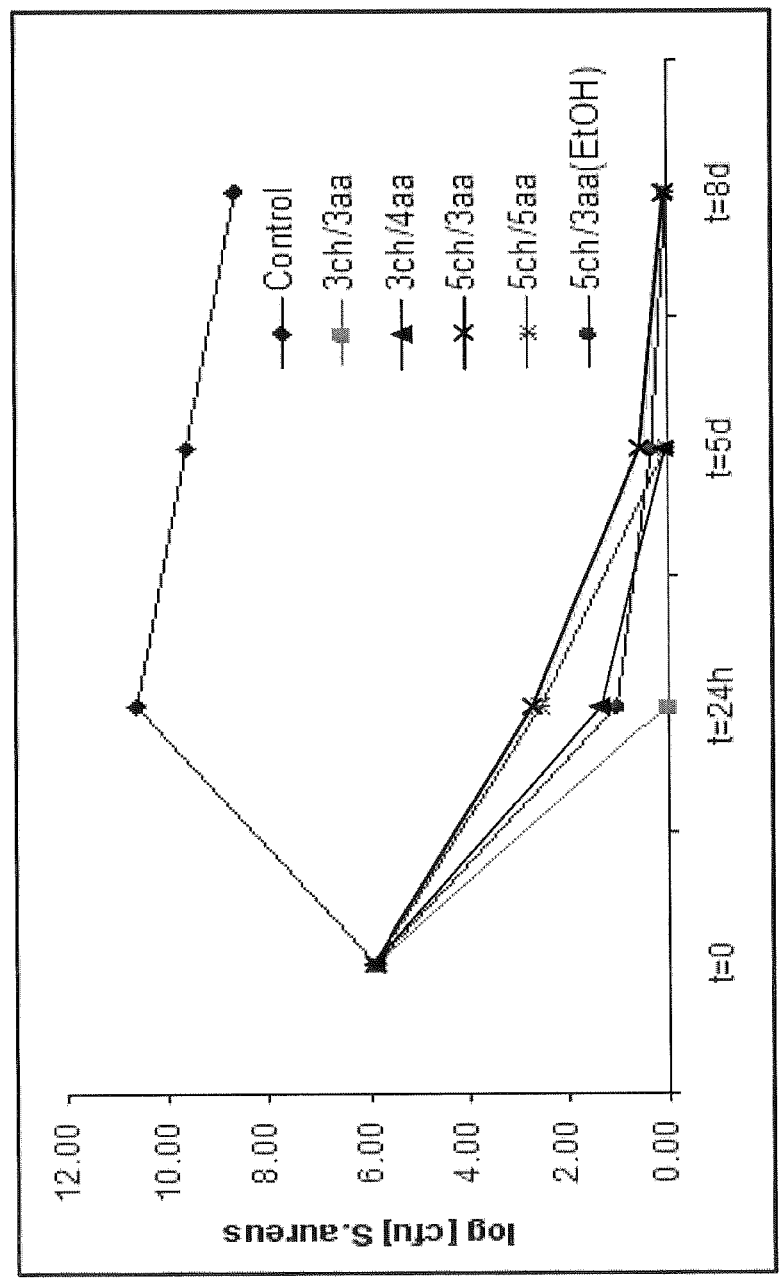
FIG. 10 summarizes the results of antimicrobial testing for various bone graft materials containing calcium phosphate and chitosan.

Several formulations of bone graft materials were prepared with varying amounts of chitosan and acid solution: 3% chitosan in 3% acetic acid, 3% chitosan in 4% acetic acid, 5% chitosan in 3% acetic acid, 5% chitosan in 5% acetic acid and 5% chitosan in 3% acetic acid washed with ethanol using the method described in Example 1. The bone graft materials were added to Tryptic Soy Broth (TSB) at a ratio of 0.2 g of material per ml of broth. Staphylococcus aureus was added to the bone graft material/broth mixture at a target concentration of $1 \times 10^6$ cfu/ml and incubated at 37° C. for up to 8 days. An aliquot of each sample was taken at 0 hour, 24 hour and 5 days, and 8 days, serially diluted, and plated onto agar plates. Bacterial colonies were counted after 24 hours. A sample containing Staphylococcus aureas without bone graft material was used as a control. FIG. 10, which summarizes the results of the plate count, demonstrates that all bone graft materials exhibit bactericidal properties within 24 hours with no bacterial recovery at least through 8 days.

Example 4

Hemostasis Testing

Several different formulations of bone graft materials were prepared by adding each of the components into a dual syringe with a luer connector and using the plunger to push the contents back and forth until mixed well, generally at least 20 pushes. The various formulations prepared are listed in Table 2 below.

TABLE 2

| Material | Efficacy |
|---|---|
| 55% collagen gelatin mixture; 45% chitosan mixture | Slight seeping under the material |
| 67% Vitagel; 1.5% chitosan solution | Appeared to clot before material ran off tubing |
| 0.5 g Knox gelatin; 6 mL chitosan solution | Stayed on wound, very absorbent |
| 43% chitosan mixture; 57% collagen mixture | Appeared to clot before material ran off tubing |
| Chitosan alginate spheres suspended in collagen | Good hemostasis once kept on wound |

Figure 11:
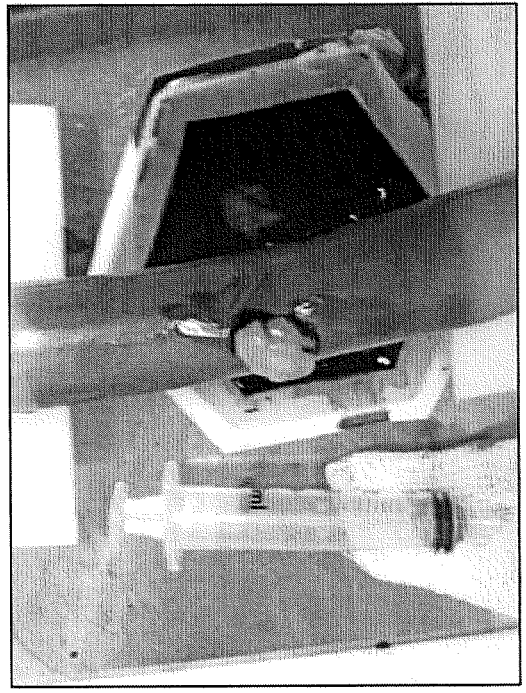
FIG. 11 contains images taken during the hemostasis study of various formulations containing chitosan.
Figure 11:
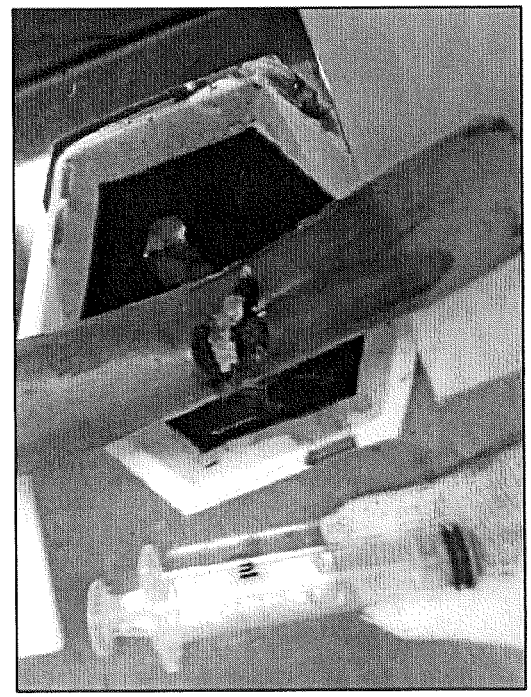

Each the formulations was tested for their hemostatic properties by simulating an injury to a blood vessel. To perform this test a cut was made in a tubing though which pigs blood was being pumped through. To test for hemostatic properties, each of the bone graft materials was applied to the cut in the tubing, while blood was pumping, to determine if the bone graft material could cause the blood to clot and prevent leakage of the blood out of the cut in the tubing. Observations regarding the clotting capabilities were made and summarized in Table 2 above. FIG. 11 contains two photograph images taken during this study. The image on the left in FIG. 11 is a picture taken of the formulation containing Knox gelatin and chitosan solution, while the image on the right is a picture of the formulation containing chitosan alginate spheres in collagen. The results indicate that all formulations containing chitosan, which can be used as precursors for the bone graft materials described herein, exhibit a certain degree of hemostasis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for preparing a biocompatible bone graft material comprising calcium phosphate, chitosan, and, optionally, collagen comprising:
   making a solution of acid in water;
   adding chitosan to the acid solution to create a slurry;
   incubating the slurry for 0.5 hour to about 5 days;
   optionally, adjusting the pH of the slurry with a base to a pH of 4 to 8;
   adding calcium phosphate and, optionally, collagen to the slurry to create a second slurry;

incubating the second slurry for 1 hour to about 24 hours to form an incubated second slurry;

drying the incubated second slurry to form a biocompatible bone graft material; and, optionally, washing the biocompatible bone graft material.

2. The method of claim 1, wherein the concentration of the acid in water is about 1% to about 20% volume by volume.

3. The method of claim 1, wherein the concentration of chitosan in the acid solution is about 0.5% to about 20% weight by volume.

4. The method of claim 1, wherein the concentration of the chitosan in the acid solution is about 0.5% to about 10% weight by volume.

5. The method of claim 1, wherein the concentration of the chitosan in the acid solution is about 1% to about 5% weight by volume.

6. The method of claim 1, wherein the slurry is incubated at a temperature of about room temperature to about 70° C.

7. The method of claim 1, wherein the second slurry contains a ratio of calcium phosphate to chitosan-acid slurry of about 0.01 grams per ml to about 1 gram per ml.

8. The method of claim 1, wherein the second slurry contains a ratio of calcium phosphate to chitosan-acid slurry of about 0.01 grams per ml to about 0.5 grams per ml.

9. The method of claim 1, wherein the second slurry contains a ratio of calcium phosphate to chitosan-acid slurry of about 0.025 grams per ml to about 0.25 grams per ml.

10. The method of claim 1, wherein the drying is selected from the group consisting of vacuum drying, air drying, and freezing and lyophilizing.

11. The method of claim 1, wherein the collagen is added to the slurry to create the second slurry.

12. The method of claim 1, wherein the incubating of the slurry is for about 4 hours to about 3 days.

13. The method of claim 12, wherein the incubating of the slurry is for about 4 hours to about 24 hours.

14. The method of claim 1, wherein the incubating of the second slurry is for about 1 hour to about 5 hours.

15. The method of claim 1, further comprising wetting the biocompatible bone graft material with a fluid to form a flexible, moldable or flowable composition.

\* \* \* \* \*